United States Patent [19]

Brewer et al.

[11] Patent Number: 4,724,208

[45] Date of Patent: Feb. 9, 1988

[54] PROCESS FOR THE PRODUCTION OF SOLUTION STABLE ALPHA-AMYLASE AND LIQUID ALPHA-AMYLASE PRODUCED THEREBY

[75] Inventors: Jack W. Brewer; Chong Y. Kim; Curtis J. Montgomery; Jayarama K. Shetty, all of Elkhart, Ind.

[73] Assignee: Miles Laboratories, Inc., Elkhart, Ind.

[21] Appl. No.: 794,282

[22] Filed: Nov. 4, 1985

[51] Int. Cl.[4] .......................... C12N 9/96; C12N 9/28; C12N 9/56; C12R 1/10

[52] U.S. Cl. .................................... 435/188; 435/202; 435/222; 435/836

[58] Field of Search ...................... 435/188, 202, 222; 252/174.12, DIG. 12

[56] References Cited

U.S. PATENT DOCUMENTS

| | | | |
|---|---|---|---|
| 3,272,717 | 9/1966 | Fukumoto et al. | 435/202 |
| 3,661,786 | 5/1972 | Desforges | 435/188 X |
| 4,519,934 | 5/1985 | Eilertsen et al. | 435/188 X |

OTHER PUBLICATIONS

Translation of Biokhimiya, vol. 44, No. 6, pp. 1084–1092, Jun. 1979.

Primary Examiner—Lionel M. Shapiro
Attorney, Agent, or Firm—Jerome L. Jeffers; Jennifer L. Skord

[57] ABSTRACT

This invention contemplates a novel process for the preparation of solution stable alpha-amylase obtained from *Bacillus licheniformis*, and to the high potency liquid enzyme product prepared by this process. Typically, the enzyme-containing solution from a fermentation is concentrated and starch is added to the concentrate. Alternatively, a precipitation agent such as salt is added to the solution, and a cake containing the enzyme precipitates. The cake is then contacted with an aqueous solution containing starch to extract the enzyme out of the cake to provide a stable liquid enzyme product.

20 Claims, No Drawings

PROCESS FOR THE PRODUCTION OF SOLUTION STABLE ALPHA-AMYLASE AND LIQUID ALPHA-AMYLASE PRODUCED THEREBY

This invention relates to a novel process for the preparation of a substantially solution stable enzyme product containing alpha-amylase from *Bacillus licheniformis* and a starch, preferably maltodextrin.

BACKGROUND OF THE INVENTION

Enzymes are biocatalysts which regulate many of the biochemical reactions that occur naturally in living organisms. Enzymes are used in many fields, such as in the tanning, detergent, food and pharmaceutical industries. In the traditional method of producing enzymes, an enzyme precipitate is dissolved in water. High potency enzyme-in-water solutions (concentrated solutions having high enzyme activity), however, may be storage unstable; the enzyme precipitates out of solution and/or is heat sensitive. U.S. Pat. No. 3,242,056 discloses the use of aqueous polyol solutions to help prevent thermal instability of lysozyme. U.S. Pat. No. 4,497,897 discloses a stable liquid proteinase from Subtilisin Carlsberg containing propylene glycol, calcium ion and carboxylate salt. U.S. Pat. No. 4,519,934 discloses a stable liquid alpha-amylase from *Bacillus licheniformis* dispersed in propylene glycol.

A liquid enzyme product comprising alpha-amylase from *Bacillus licheniformis* in aqueous solution is desirable since it can be put directly to its industrial use, such as in liquid detergents, without the inconvenience of first resolubilizing a dry, enzyme precipitate in water and/or without the concern of solvent (e.g. propylene glycol) compatibility. Also, enzyme dust from a dry product is avoided. Thus, researchers have long sought methods to maintain this enzyme in aqueous solution, particularly high potency (highly concentrated) solutions. Although the prior art mentioned in the paragraph above shows the use of various solvents (e.g. propylene glycol), never is there obtained an aqueous enzyme product of high enzyme activity where this enzyme stays in solution.

For instance, alpha-amylase can be obtained from culturing various microorganisms, such as *Bacillus subtilis* or *Bacillus licheniformis* in a suitable nutrient medium. *B. subtilis* produces alpha-amylase that is physically stable, i.e. the enzyme will not appreciably precipitate out of an aqueous solution even when the activity is 3 million MWU/ml (Modified Wohlgemuth Units per milliliter), or higher. However, these alpha-amylase solutions are heat sensitive, and maltodextrin is added to enhance thermostability. Similarly, Klesov et al in "Substrate Thermostabilization of Soluble and Immobilized Glucoamylase", Department of Chemistry, Moscow State University, Biokhimiya, Vol. 44 (6), pages 1084–92 (1979), disclose thermostabilization of a solution of glucoamylase from *Aspergillus niger* with maltodextrin. On the other hand, alpha-amylase obtained from *Bacillus licheniformis* is heat stable (see for instance, Volesky et al, Microbial Enzymes: Production, Purification, and Isolation, Volume 2, Issue 2, page 120, 1985) but it is not especially physically stable in an aqueous solution at high concentrations.

STATEMENT OF THE INVENTION

The present invention provides for a process as follows. In combination with the production of heat stable alpha-amylase by the fermentation of *Bacillus licheniformis* to provide a fermentation broth containing the enzyme and solid waste products from the fermentation, the improvement comprising: (a) adding to the fermentation broth a starch which will, when added in sufficient quantity inhibit enzyme-enzyme agglomeration thereby enhancing the solubility of the alpha-amylase in aqueous solution.

DETAILED DESCRIPTION OF THE INVENTION

None of the literature, however, suggests or discloses the present novel discovery of employing a starch to prepare an aqueous product having high enzyme activity wherein the enzyme is heat stable alpha-amylase from *B. licheniformis*, and thus the effect of the addition of a starch on the stabilization of aqueous alpha-amylase solutions having activities up to approximately 1,000,000 MWU/ml was studied.

Accordingly, it is an object of the present invention to provide a substantially solution stable alpha-amylase formulation wherein the alpha-amylase is obtained from *B. licheniformis*. By "substantially solution stable" is meant that the enzyme staying in solution is favored, as opposed to the enzyme precipitating out of solution, when that solution is potent, i.e. has a high enzyme concentration wherein the activity is at least 350,000 MWU/ml. By adjusting the amount of starch, very concentrated solutions having an activity of 1,000,000 MWU/ml or even higher, which are substantially solution stable, can be obtained.

The present liquid formulation may contain an amylase other than heat stable alpha amylase from *B. licheniformis* and/or a protease. Various microorganisms that produce amylases and/or proteases include, but are not limited to, *Bacillus subtilis*, *B. licheniformis*, *B. stearothermophilus*, and *B. amyloliquefaciens*. Also, the present formulations are preferably intended to be used in a detergent and thus may contain from about 0% to about 80% of a detergent surfactant from the group of amphoteric, anionic, cationic, nonionic, zwitterionic, or semipolar-nonionic surfactants or a mixture thereof. Such detergents are well known and examples of some detergents useful with the present liquid enzyme formulations are those described in U.S. Pat. No. 4,318,818 (Letton, et al) and U.S. Pat. No. 4,111,855 (Barrat, et al), the disclosures of which are herein incorporated by reference.

The chart below shows a preferred embodiment as compared to conventional processing. This chart as intended for illustrative purposes only and is not to be construed as required for teaching how to practice the present invention.

| CHART |
| --- |
| (A) Fermentation (Biomass Separation) |
| (B) Culture Filtrate (PM-2 Membrane) |
| (C) UF Concentrate |

|  (D)(i) | or | (D)(ii) |
| --- | --- | --- |
| Precipitation Method to Obtain Cake | | Vacuum Evaporation Method to Obtain Concentrate |

CHART -continued

| (E')(i) Extract Enzyme From Cake into Water (Adjust to pH 8, Store at 10° C. for 18-24 hours) (Filtration) | or | (E')(ii) Continued Evaporation | (E)(i) Extract Enzyme From Cake into Water Containing Starch | or | (E)(ii) Stabilization by adding Starch pH 6.5 |
|---|---|---|---|---|---|
| (F') Enzyme Cake Product | | | (F) Liquid Final Product | | |
| (G) Extract Enzyme from Cake into Water Containing Starch, pH 6.5 | | | | | |

A simple process to produce a substantially stable, high potency, aqueous alpha-amylase preparation is described in the chart. The method comprises (A) conducting a fermentation, (B) separating the biomass from the fermentation broth containing the enzyme by filtration, (C) ultrafiltering (UF) to obtain an enzyme concentrate, (D) either (i) precipitating a cake containing the enzyme or (ii) conducting further concentration by vacuum evaporation or additional ultrafiltration, and then (E) either (i) extracting the precipitated enzyme out of the cake and into an aqueous solution by reslurrying the cake in the solution or by circulating the solution through the cake wherein the extracting solution contains starch or starch is added to the extract or (ii) adding starch directly to the concentrate, to obtain (F) an aqueous starch-containing final product. In conventional processing, step (E') instead consists of (i) slurrying the cake in water to extract the enzyme therefrom or consists of (ii) continued evaporation. Then an enzyme-containing cake reprecipitates and excess mother liquor is filtered off leaving a dry enzyme product (F'). Alternatively, the present invention could be employed after steps (E') and (F') by extracting the enzyme from this precipitated cake into an aqueous solution containing starch (G).

After enzyme production, the solids (biomass from fermentation) may be removed from the whole fermentation broth to provide an enzyme-containing solution by any standard technique such as filtration and/or centrifugation. Next, the cell free enzyme-containing solution is preferably concentrated between about 1 and 10 fold by any concentration means such as ultrafiltration and/or evaporation. A starch or an aqueous solution containing a starch is added to the solution or concentrate in an amount from about 0.1% to 50% w/v (weight/volume), more preferably about 3% to 15% w/v, of starch to the enzyme-containing solution or concentrate.

In a desired embodiment, prior to addition of the starch, a precipitation agent may be added to the cell free enzyme-containing solution (or concentrate) causing a cake containing the enzyme to precipitate out. Well known precipitation agents are the low molecular weight organic solvents, such as methanol, ethanol, isopropanol, 1-propanol, n-butanol, tert-butanol, and a mixture thereof or salts such as sodium sulfate, ammonium sulfate, and a mixture thereof. It is intended here that the term "cake" should encompass the term "slurry" to include those instances where the cake is so wet that it would be considered a slurry. If there is excess mother liquor, it can be removed from the slurry or cake by employing any of several methods such as ordinary filtration, suction filtration, gravity sedimentation, or centrifugation. Then an aqueous solution containing from about 0.1% to 50% w/v, more preferably about 3% to 15% w/v, starch in water may be prepared and employed to dissolve or extract the enzyme from the cake. Also, the extraction of the enzyme from the cake may be carried out with water, and then the starch added in an amount of about 0.1% to 50% w/v to the extract.

In another embodiment, the solid waste products (i.e. biomass from fermentation) are not separated from the fermentation broth after the enzyme production. Rather, the starch or aqueous solution of starch is added directly to the whole fermentation broth. This helps maintain the enzyme in solution so that when the solid waste products are removed, less of the enzyme is lost in the solids. The starch should be added in an amount of from about 0.1% to 50% weight to volume to the whole fermentation broth.

Any starch may be employed in the present invention, and this is meant to include also the derivatized starches, such as acetylated starch or starch glycolate. The starch may be a substrate for the enzyme. In general, enzymes that exhibit their maximum activity at an elevated temperature, i.e. such as 60° C., do not act appreciably on a substrate unless there is some heating. More particularly, the alpha amylase of *B. licheniformis* essentially does not begin to hydrolyze a starch substrate until the temperature is approximately 40° C., with substantial hydrolyzing not occurring until approximately 60° C. Thus, the starch substrate will not be appreciably degraded under typical, ambient storage conditions. The starch substrates preferred in the present invention are corn syrup and maltodextrins. Especially preferred are maltodextrins. A source of maltodextrin in MALTRIN®, a hydrolyzed corn product (cereal solids) supplied in various dextrose equivalents, for example by Grain Processing Corporation of Muscatine, Iowa. MALTRIN is a bland, white, food grade carbohydrate with very desirable bulking characteristics. It has a low sweetness, is readily soluble in water and is resistant to clumping.

For instance, a typical analysis of MALTRIN-100 is:

| Typical Chemical and Physical Data | |
|---|---|
| Dextrose Equivalent | 9.0–12.0 |
| Moisture, % Maximum | 6.0 |
| pH, 20% Solution | 4.0–4.7 |
| Form | White Powder |

| Typical Carbohydrate Profile (dry basis) | |
|---|---|
| Monosaccharides | 1% |
| Disaccharides | 4% |
| Trisaccharides | 6% |
| Tetrasaccharides | 5% |
| Pentasaccharides, & Above | 84% |

It has been found that a concentration of about 3% to 15% w/v of maltodextrin is most advantageous in maintaining the enzyme in solution.

Moreover, it has been surprisingly discovered that there is an inverse correlation between the dextrose equivalent (DE) of the maltodextrin and the maintenance of solubilization of the enzyme. In other words, the lower the DE of the maltodextrin, the more the enzyme tends to stay in solution. Preferably, the DE is about 35 or less, more preferably less than about 25. This discovery is illustrated in Example IV below.

Other starches with other dextrose equivalents may also be advantageously employed. The exact mechanism is not known, but it is theorized that any starch will work due to the formation of a stable enzyme/substrate complex.

In the preferred embodiment, either after or before the addition of the starch, the pH of the enzyme-containing solution is adjusted to a level at or above the isoelectric point of the enzyme. The pH should be in a range from approximately 4.0 pH units above the isoelectric point down to approximately the isoelectric point. Preferably, the pH is no more than approximately 3.0 units above the isoelectric point. The isoelectric point of alpha-amylase varies between 4.8 and 5.5, and at such an acidic pH, the enzyme will stay in solution. However, keeping the pH that low is not an alternative for storage of the alpha-amylase solution because the acidity will denature the enzyme. In the most preferred embodiment in which the enzyme is TAKA-THERM ® (supplied by Miles Laboratories, Inc., Elkhart, Ind.), a heat stable alpha-amalyse obtained from the fermentation of a mutant strain of *Bacillus licheniformis*, the pH should be between approximately 5.5 and 9.0, more preferably between approximately 6.0 and 8.2. It has been discovered that the optimum pH for the preferred embodiment with TAKA-THERM is between approximately 6.5 and 8.0. The preferred agents for adjusting the pH are well known in the art of enzyme chemistry and examples are bases such as NaOH and KOH, and acids such as hydrochloric and acetic.

Alpha-amylase activity was measured in the Examples by determining the hydrolysis of soluble starch using blue value reduction of starch-iodine complex as described in the Manual of Liquefying Alpha-Amylase Assay which is a modification of the method disclosed by Wohlgemuth in Biochem. 29:1 (1908). In a typical run, 5 ml of 2% soluble starch buffered at pH 5.4 and 4 ml water are incubated with 1 ml properly diluted enzyme in a water bath maintained at 40° C. At timed intervals (5–30 minutes from the addition of enzyme) aliquots (1 ml) were withdrawn and injected into a tube containing 5 ml of dilute iodine solution and mixed by inversion. The developed color was then compared in a comparator to monitor the approach of the reaction end point. The enzyme activity was calculated as Modified Wohlgemuth Units per milliliter (MWU/ml).

One Modified Wohlgemuth Unit (MWU) is that activity which dextrinizes one ml of soluble starch to a defined blue value in thirty minutes under the conditions of the assay. For the calculation, it is assumed the density is that of water, and thus activity per milliliter is assumed to be equivalent to activity per gram. The calculation is:

$$MWU/ml = MWU/g = \frac{100 \times 30}{T \times W} = \frac{3000}{T \times W}$$

where
100 = Milligrams starch in each incubation mixture
30 = Defined dextrinizing time in minutes
$T$ = Time in minutes required to reach end point
$W$ = Weight in grams of enzyme added to incubation mixture in one milliliter aliquot of enzyme dilution A schematic representation of the theory of stabilization of alpha-amylase at high concentrations using maltodextrins as the starch substrate is as follows. It has been unexpectedly discovered that factors which decrease the concentration of the free enzyme in solution, also prevent the aggregation of the enzyme at high enzyme activity. Removal of water from a dilute enzyme solution tends to favor enzyme-enzyme interactions instead of enzyme-water interactions. The increased enzyme-enzyme interactions thus cause the enzyme to associate through non-covalent attraction resulting in the precipitation of the enzyme.

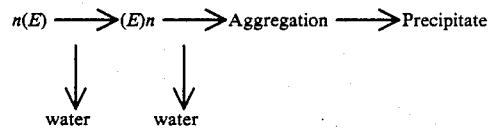

It has been found that the addition of starch (S) either to the extract of enzyme or during concentration of the enzyme circumvents the insolubilization of the enzyme at high concentrations, as represented by the following formula.

$$n(E) + m(S) \rightarrow (ES)_x + S_{(n-m)} + E_{n-x}, \text{ if } n > m$$

Under equilibrium, the solution generally comprises x moles of enzyme/starch complex (ES), the starch ($S_{n-m}$) and free enzyme ($E_{n-x}$).

The experimental data indicates that in the absence of any starch the precipitation of the enzyme occurred when concentration of the free enzyme ($E_{n-x}$) was more than 350,000 MWU/ml activity based on weight of the enzyme in the solution.

The embodiments illustrated in the Examples below all employ TAKA-THERM, a heat stable alpha-amylase obtained from *B. licheniformis*, and the invention is not intended to be limited thereby.

Fermentation of *Bacillus licheniformis* to Produce Heat Stable Alpha-Amylase (TAKA-THERM)

A fermentation media suitable for culturing a strain of *B. licheniformis* to produce heat stable alpha-amylase can be prepared for a 1000 liter fermentor as follows:

| | |
|---|---|
| Calcium Chloride Dihydrate (Flake) | 0.2–1.0 kg |
| Mono- and Dipotassium Phosphate | 15–24 kg |
| Ammonium Sulfate | 2–7 kg |
| Suitable Carbon Source | 100–200 kg |
| Cotton Seed Meal | 25–40 kg |
| Soy Media (soy meal) | 30–50 kg |
| Mazu DF 6000* | 8–13 L |
| Water added to | 1,000 L total volume |

*An organic defoamer supplied by Mazu Company, the major ingredients of which are polypropylene glycol and silicone.

The media was inoculated with viable cells of a strain of *Bacillus licheniformis* and allowed to ferment for 70–90 hours at 40°–50° C. while maintaining the pH approximately neutral. After this fermentation, the media may be flocculated by a suitable flocculant to aid in biomass removal. The biomass may be removed by means such as centrifugation or filtration, and the liquid passed through a drum filter to polish it and thereby provide a cell-free solution (primary culture filtrate or supernatant). Typically, the drum filter is precoated with filter aid such as Superaid ® to polish (i.e. clarify) the primary culture filtrate or supernatant.

In a preferred embodiment, the primary culture filtrate may be concentrated by ultrafiltration, such as with a PM-10 membrane (molecular weight cut-off 10,000) and/or by vacuum. Then, the enzyme may be quantitatively precipitated (pH 6-8) from the concentrated culture filtrate in the form of an enzyme-containing cake preferably by the addition of 20% w/v sodium sulphate, 28% w/v ammonium sulphate, or 80% (v/v) ethanol, which is followed by extracting the enzyme from the cake with water, and adding maltodextrin to the extract.

Example I

An alpha-amylase primary culture filtrate as described above which had been polished by passing it through a drum filter coated with Superaid ® was concentrated 7-fold by ultrafiltration using a Romicon ® 20HF-4 filter apparatus with a 10,000 molecular weight cut-off membrane at 10° C., and divided into several aliquots. The pH of each aliquot was adjusted to 7.6 with 20% w/v aqueous KOH. Then Maltrin-20 was added to several samples in varying % w/v, and the samples stirred well for uniform mixing. A few samples were kept as controls (0% w/v Maltrin-20). Next, each was further concentrated by vacuum at 35° C. with a rotating evaporator (Brinkman-Buchi Rotovapor ®) to the desired amylase activity and Maltrin concentration for the particular sample. All samples were preserved from microbial contamination by adding 0.5% w/v potassium sorbate followed by storage for one month at 25° C. After the specified time, the samples were centrifuged. The amount of enzyme (whether initial, remaining in the supernatant, or precipitated) can be determined by measuring the activity in MWU/ml as described above. Thus, the amount of enzyme in the supernatant was measured and subtracted from the initial amount of enzyme to give the amount of enzyme lost in the precipitate, which was converted to the percent enzyme precipitated by using the formula 100×(enzyme precipitated/initial enzyme). The results are summarized in Table I below.

TABLE I

Effect of Maltrin-20 on the Extent of Precipitation of Alpha-Amylase During Storage at 25° C. for 1 Month

| Sample # | Initial MWU/ml | Concentration (% w/v) Maltrin-20 | % Enzyme Precipitated |
|---|---|---|---|
| 1. | 1,043,478 | 0.00* | 93.5 |
| 2. | 1,043,478 | 2.11 | 28.5 |
| 3. | 960,000 | 3.70 | 37.8 |
| 4. | 1,043,478 | 6.34 | 25.6 |
| 5. | 1,180,378 | 7.40 | — |
| 6. | 779,721 | 0.00* | 88.8 |
| 7. | 789,474 | 2.6 | 79.4 |
| 8. | 845,522 | 5.4 | 16.4 |
| 9. | 895,522 | 9.0 | 17.6 |
| 10. | 845,070 | 11.4 | 25.4 |
| 11. | 845,070 | 13.6 | 22.0 |
| 12. | 716,418 | 0.00* | 85.2 |
| 13. | 872,727 | 2.38 | 21.0 |
| 14. | 979,592 | 4.54 | 68.8 |
| 15. | 786,885 | 6.25 | 16.7 |
| 16. | 786,885 | 8.33 | 17.8 |
| 17. | 872,727 | 11.36 | 25.0 |
| 18. | 640,000 | 0.00* | 80.9 |
| 19. | 551,724 | 2.2 | 71.1 |
| 20. | 578,313 | 4.2 | 39.8 |
| 21. | 578,313 | 5.73 | 54.0 |
| 22. | 516,129 | 8.00 | 14.4 |
| 23. | 558,140 | 10.00 | 15.1 |
| 24. | 470,588 | 0.00* | 54.8 |

TABLE I-continued

Effect of Maltrin-20 on the Extent of Precipitation of Alpha-Amylase During Storage at 25° C. for 1 Month

| Sample # | Initial MWU/ml | Concentration (% w/v) Maltrin-20 | % Enzyme Precipitated |
|---|---|---|---|
| 25. | 452,830 | 2.1 | 68.2 |
| 26. | 452,830 | 4.2 | 45.2 |
| 27. | 470,588 | 6.3 | 14.2 |
| 28. | 452,830 | 8.4 | 14.3 |
| 29. | 489,796 | 11.25 | 15.4 |
| 30. | 369,231 | 0.00* | 56.0 |
| 31. | 421,053 | 2.74 | 14.0 |
| 32. | 406,780 | 4.25 | 12.7 |
| 33. | 380,952 | 6.57 | 14.5 |
| 34. | 380,952 | 8.76 | 13.0 |
| 35. | 393,443 | 10.96 | 11.9 |

*Samples 1, 6, 12, 18, 24 and 30 were controls.

The results set out in Table I indicate that Maltrin inhibited the precipitation of the enzyme in a concentrated culture filtrate. However, the enzyme is not maintained in a high potency solution as well as it is in the preferred embodiment described in Example III below.

Example II

The procedure of Example I was followed except the order of concentration, pH adjustment, and Maltrin addition was differed. The entire culture filtrate was concentrated 7-fold by ultrafiltration, and then evaporated to a concentration of approximately 700,000 MWU/ml. The pH of the concentrate was then adjusted to 7.6 and the concentrate divided into 4 portions. Maltrin-20 was added to each in various concentrations. The samples were stirred moderately at 25° C. for 40 hours and then centrifuged. The percent enzyme lost in the precipitate was calculated in the same manner as in Example I. The results are summarized in Table II below.

TABLE II

Effect of Maltrin-20 at 700,000 MWU/ml

| % w/v Maltrin-20 | % Enzyme Precipitated |
|---|---|
| 0.00 | 84 |
| 2.0 | 74 |
| 4.0 | 48 |
| 8.0 | 6.2 |

From the Table, it can be seen that various amounts of Maltrin-20, up to 8.0% w/v, demonstrated a drastic decrease in loss of enzyme due to precipitation. However, the activity is not maintained in a high potency solution as well as it is in the preferred embodiment in Example III below.

Example III

An alpha-amylase solution concentrated by ultrafiltration 4 fold with a PM-10 membrane followed by Na₂SO₄ precipitation (20% w/v) as described above was used for this Example.

Since sodium sulfate was used as the precipitating agent, heating above room temperature, i.e. to approximately 30° C., was carried out to alleviate clumping of the sodium sulfate. Filteraid FW-6 (1% w/v) was added and an enzyme-containing cake was collected by vacuum filtration. The enzyme-containing cake was removed from the filter apparatus and reslurried in minimum amount of water to dissolve the enzyme therefrom. The slurry was filtered to produce a concentrated enzyme solution, and then adjusted with water to a high initial enzyme concentration as determined by a measured activity of 1,000,000 MWU/ml and further divided into 7 aliquots. Maltrin-250 (powdered) was added to 6 of the aliquots in the amount of 1%, 2%, 3%, 4%, 5% and 10% w/v, and one aliquot was kept as control (0% Maltrin-250). After the addition, the samples were stirred well for uniform mixing and the pH was adjusted to pH 8.0 with KOH. The initial activity was corrected for the dilution due to the addition of Maltrin, i.e. proper blanks containing the respective amounts of Maltrin-250 were also prepared to eliminate any error due to the effect of Maltrin on the assay. All samples were stored at 10° C. for 24 hours. After the specified time, the samples were filtered. As mentioned above, the amount of enzyme is determined by measuring the activity. Thus, the amount of enzyme in the filtrate was measured, and subtracted from the corrected initial amount of enzyme to give the enzyme lost in the precipitate which was converted to the percent enzyme precipitated using 100×(enzyme precipitated/corrected initial enzyme). The results are summarized in the Table III below.

TABLE III

Effect of Maltrin-250 Concentration on the Aqueous Stabilization of Alpha-Amylase at High Initial Enzyme Concentration of 1,000,000 MWU/ml, pH 8.0, with storage at 10° C. for 24 Hours

| Sample # | Concentration, Maltrin-250 (% w/v) | Percent Enzyme Precipitated |
|---|---|---|
| 1. Control | 0 | 80 |
| 2. | 1 | 45 |
| 3. | 2 | 18 |
| 4. | 3 | 0 |
| 5. | 4 | 0 |
| 6. | 5 | 0 |
| 7. | 10 | 0 |

The aqueous enzyme solution was much purer than the concentrated culture filtrate as described in Example I above, as the $Na_2SO_4$ precipitation removed impurities. Thus, no more than 3% w/v Maltrin was needed to maintain essentially all the enzyme activity in solution. As can be seen, no enzyme precipitated when the concentration of Maltrin-250 was 3% w/v and above, and thus 100% of the amylase as measured by its activity remained in the filtrate.

Example IV

Example III was repeated except this time the amount of Maltrin added was kept constant and its dextrose equivalent was varied. Thus, the effect of degree of polymeriation (DP) of maltodextrins on the stabilization of alpha-amylase at high activity was studied. Maltodextrins with varying dextrose equivalents (DE) were added in an amount of 1% w/v to 8 aqueous, concentrated, alpha-amylase aliquots containing 1,000,000 MWU/ml initial activity. The pH of each sample was adjusted to 8.0 with KOH and the activity corrected for the addition of Maltrin. The samples were stored at 10° C. for 24 hours. After the specified time, the stored samples were filtered. The filtrate was assayed for alpha-amylase activity and the percent enzyme precipitated was calculated in the same manner as in Example III. The results are summarized in the Table below.

TABLE IV

Effect of DE on the Stabilization of Alpha-Amylase at High Initial Enzyme Concentration of 1,000,000 MWU/ml with Storage at 10° C. for 24 Hours

| Sample # | Starch Substrate | Measured DE | % Enzyme Precipitated |
|---|---|---|---|
| 1. | Maltrin-040 | 5.2 | 40.0 |
| 2. | Maltrin-100 | 11.4 | 41.5 |
| 3. | Maltrin-150 | 16.1 | 41.5 |
| 4. | Maltrin-200 | 22.5 | 45.5 |
| 5. | Maltrin-250 | 23.6 | 45.5 |
| 6. | Maltrin-365 | 35.7 | 51.0 |
| 7. | Maltose | 68.0 | 82.0 |
| 8. | Glucose | 100.0 | 85.0 |
| 9. Control | None | — | 80.6 |

The results in Table III indicate that the stabilization of the enzyme was increased with decreasing DE of maltodextrin. Also, the addition of maltose or glucose did not effect any decrease in enzyme precipitated as compared to the control, but rather effected a slight increase.

Comparative Example A (No Maltrin)

A concentrated alpha-amylase solution obtained by the ultrafiltration and $Na_2SO_4$ precipitation method (20% w/v) as described in Example II was used for this Example.

The pH of the concentrated enzyme solution was adjusted with KOH to pH 8.0, and then the solution was further divided into 3 samples. Then the initial concentration of enzyme of each of the samples was adjusted with water to an activity of 1,000,000 MWU/ml, 700,000 MWU/ml and 350,000 MWU/ml, respectively. Each of the 3 samples was then divided into 4 parts and stored at 5° C., 10° C., 24° C. and 37° C. for 18 hours. After the specified time, the samples were filtered using Whatman No. 3 filter paper and the amount of enzyme in the filtrate was determined by measuring the activity and the percent enzyme precipitated was calculated using 100 (initial enzyme-filtrate enzyme)/initial enzyme. The results are reported in Table A below.

TABLE A

Effect of Temperature and Initial Enzyme Concentration on the Enzyme Precipitated at pH 8.0, with Storage at Various Temperatures for 18 Hours

| Initial Enzyme Activity MWU/ml | Incubation Temp., °C. | Percent Enzyme Precipitated After 18 Hours at pH 8.0 |
|---|---|---|
| 1. 1,000,000 | 5 | 81.3 |
| | 10 | 80.0 |
| | 25 | 80.7 |
| | 37 | 75.0 |
| 2. 700,000 | 5 | 44.3 |
| | 10 | 45.6 |
| | 25 | 41.4 |
| | 37 | 23.8 |
| 3. 350,000 | 5 | 4.8 |
| | 10 | 7.3 |
| | 25 | 7.3 |
| | 37 | 0.0 |

The results in the above table clearly demonstrate the relationship between initial enzyme and the extent of enzyme precipitation in the absence of Maltrin. Storage of aqueous enzyme solution containing 1,000,000 MWU/ml high initial activity at pH 8.0 for 18 hours resulted in 75–81.3% enzyme precipitated, whereas a low initial activity of 350,000 MWU/ml resulted in only a 7.3% or less loss of enzyme in the precipitate. In other words, as the potency of the enzyme solution increases, i.e. the solution has a higher concentration of alpha amylase, then the tendency is for the enzyme to precipitate rather than stay in solution.

Comparative Example B (No Maltrin)

Example A was repeated except this time the activity was kept constant and the pH was varied.

An aliquot as in Example A of the concentrated solution that had been adjusted with water to a high initial activity of 1,000,000 MWU/ml was divided into 6 aliquots. Each was adjusted with KOH to pH 5.5, 6.5, 7.5, 8.5, 9.5 and 10.5, respectively, and stored at 5° C. for 18 hours. After the storage, the samples were filtered through Whatman #3 paper and the remaining enzyme in the filtrate was determined and then the percent enzyme precipitated calculated in the same manner as in Example A. The results are summarized in Table B below.

TABLE B
Effect of pH on the Alpha-Amylase
Enzyme Precipitated at High Initial Activity
with Storage at 5° C. for 18 Hours

| Sample # | pH | Percent Alpha-Amylase Precipitated |
|---|---|---|
| 1. | 5.5 | 0 |
| 2. | 6.5 | 9.0 |
| 3. | 7.5 | 65.0 |
| 4. | 8.5 | 80.0 |
| 5. | 9.5 | 76.5 |
| 6. | 10.5 | 52.0 |

The extent of the enzyme precipitated from the solution increased as the pH increased from pH 6.5 to pH 8.5 and reached a maximum at pH 8.5. Above pH 8.5, a decrease in the enzyme lost in the precipitate was observed which may be due to resolubilization of the precipitated enzyme at high alkaline pH. It is interesting to note that the maximum solubility of the enzyme at a high initial concentration occurred at pH 5.5, which is approaching the isoelectric point of the enzyme. Nevertheless, as mentioned above, such an acidic pH will denature the enzyme during long periods of storage.

Comparative Example C (No Maltrin)

Effect of Temperature on the Rate of Precipitation of Alpha-Amylase at pH 8.0

An aliquot of a concentrated, aqueous enzyme solution containing 1,000,000 MWU/ml initial activity as in Example B was separated into two different flasks (150 ml for each sample), except the pH of each was adjusted to 8.0 using sodium hydroxide. The two samples were then stored at 10° C. and 37° C. respectively. A 10 ml aliquot was withdrawn from each flask at different intervals of time, i.e., 2.5 hours, 4 hours, 7 hours, 10 hours, 12 hours and 20 hours. Immediately after withdrawal, each aliquot was filtered through Whatman #3 paper and the filtrate was assayed for alpha-amylase. Then the percent enzyme precipitated was calculated in the same manner as in Example A. The results are summarized in Table C below.

TABLE C
Effect of Temperature on the Rate of
Precipitation of Alpha-Amylase at pH 8.0

| Time (Hours) | Percent Enzyme Precipitated | |
|---|---|---|
| | 10° C. | 37° C. |
| 2.5 | — | — |
| 4 | — | — |
| 7 | 36 | — |
| 10 | 61 | 19 |
| 12 | 75 | 40 |
| 20 | 80 | 65 |

The results in Table C indicate that the low temperature favored the precipitation of the enzyme while 37° C. favored its solubilization.

In summary with respect to Tables A, B, and C, the results clearly demonstrate the relationship of initial enzyme in the solution to the extent of enzyme lost in the precipitate at various pH's and temperatures. Removal of water from enzyme solution, i.e. making a concentrated solution of high activity, causes increased protein-protein interaction which tends to favor the aggregation of the enzyme resulting in precipitation. Comparison to Examples I, II, III and IV clearly shows that the addition of Maltrin to concentrated solutions of high activity inhibits protein-protein interaction and favors solubility of the enzyme.

We claim:

1. In combination with the production of heat stable alpha-amylase by the fermentation of *Bacillus licheniformis* to provide a fermentation broth containing the enzyme and solid waste products from the fermentation, the improvement which comprises adding to the fermentation broth a maltodextrin in sufficient quantity to inhibit enzyme-enzyme agglomeration thereby enhancing the solubility of the alpha-amylase in aqueous solution.

2. The process of claim 1, wherein the fermentation broth is treated to remove the solid waste products before the addition of the maltodextrin to provide a cell free enzyme-containing solution to which the maltodextrin is added thereby rendering an aqueous, substantially solution stable, alpha-amylase product.

3. The process of claim 2, wherein the maltodextrin is admixed with the enzyme-containing solution in an amount from about 0.1% to 50% weight/volume of maltodextrin to solution, wherein the maltodextrin is added directly, or the maltodextrin is first dissolved in $H_2O$ and the resulting aqueous solution of maltodextrin is added.

4. The process of claim 3, wherein the enzyme-containing solution is concentrated between about 1 and 10 fold and the maltodextrin is added during or after the concentration.

5. The process of claim 4, wherein before or after the addition of the maltodextrin, the pH is adjusted to a point within a range from approximately the isoelectric point of the enzyme up to approximately 4.0 pH units above the isoelectric point.

6. The process of claim 5, wherein the activity of the aqueous product is $\geq 350,000$ MWU/ml.

7. The process of claim, 1 wherein the maltodextrin has a dextrose equivalent below about 35.

8. The process of claim 2, wherein after the removal of the solid waste products to provide the cell-free enzyme-containing solution and before the addition of the maltodextrin, a precipitation agent selected from the group consisting of salts and low molecular weight organic solvents is added to the enzyme-containing solution to cause a cake containing the enzyme to precipitate, and then the enzyme is extracted from the enzyme-containing cake into (i) water followed by adding to the extract a maltodextrin in an amount of about 0.1% to 50% weight/volume of starch to water or is extracted into (ii) water containing a maltodextrin in an amount of about 0.1% to 50% weight/volume of maltodextrin to water.

9. The process of claim 8, wherein extracting the enzyme from the cake consists essentially of circulating the water or water solution of maltodextrin through the cake or reslurrying the cake in the water or water solution of maltodextrin.

10. The process of claim 8, wherein before or after the addition of the maltodextrin, the pH of the extract is adjusted to a point within a range from approximately the isoelectric point of the enzyme up to approximately 4.0 pH units above the isoelectric point.

11. The process of claim 8, wherein the salt precipitation agent is selected from the group consisting of sodium sulfate, ammonium sulfate, and a mixture thereof, and the organic solvent precipitation agent is selected from the group consisting of methanol, ethanol, 1-propanol, isopropanol, n-butanol, tert-butanol, and a mixture thereof.

12. The process of claim 8, wherein prior to addition of the precipitation agent, the enzyme-containing solution is concentrated between about 1 and 10 fold.

13. The process of claim 12, wherein the activity of the aqueous product is $\geq 350,000$ MWU/ml.

14. The process of claim 10 wherein the maltodextrin has a dextrose equivalent below about 35.

15. An aqueous, substantially solution stable, alpha-amylase product made by the process of claim 2.

16. An aqueous, substantially solution stable, alpha-amylase product made by the process of claim 12.

17. An aqueous, substantially solution stable, alpha-amylase formulation comprising heat stable alpha-amylase from *Bacillus licheniformis*, and a maltodextrin in an amount of about 0.1 to 50% w/v.

18. The formulation of claim 17, further including an amylase other than heat stable alpha amylase from *B. licheniformis*, a protease, or a mixture thereof.

19. The formulation of claim 17, further including from about 0% to about 80% of a detergent surfactant from the group of amphoteric, anionic, cationic, nonionic, zwitterionic, or semipolarnonionic surfactants, or a mixture thereof.

20. The formulation of claim 18, further including from about 0% to about 80% of a detergent surfactant from the group of amphoteric, anionic, cationic, nonionic, zwitterionic, or semipolar-nonionic surfactants, or a mixture thereof.

* * * * *